(12) United States Patent
Stockert

(10) Patent No.: US 6,592,580 B1
(45) Date of Patent: Jul. 15, 2003

(54) APPARATUS FOR THE HIGH-FREQUENCY TREATMENT OF BODY TISSUE

(75) Inventor: Rüdiger Stockert, Freiburg (DE)

(73) Assignee: Stockert GmbH, Freiburg (DE)

( * ) Notice: Subject to any disclaimer, the term of this patent is extended or adjusted under 35 U.S.C. 154(b) by 0 days.

(21) Appl. No.: 09/485,376

(22) PCT Filed: Aug. 10, 1998

(86) PCT No.: PCT/EP98/05068

§ 371 (c)(1),
(2), (4) Date: Feb. 8, 2000

(87) PCT Pub. No.: WO99/07298

PCT Pub. Date: Feb. 18, 1999

(30) Foreign Application Priority Data

Aug. 8, 1997 (DE) .......................... 197 34 506

(51) Int. Cl.⁷ ............................... A61B 18/18
(52) U.S. Cl. ......................... 606/41; 607/102
(58) Field of Search ............... 606/41–50; 607/101, 607/102, 122

(56) References Cited

U.S. PATENT DOCUMENTS

| 4,532,924 A | * | 8/1985 | Auth et al. | 606/41 |
|---|---|---|---|---|
| 5,257,635 A | * | 11/1993 | Langberg | 607/122 |
| 5,314,466 A | * | 5/1994 | Stern et al. | 606/45 |
| 6,099,524 A | * | 8/2000 | Lipson et al. | 606/41 |
| 6,149,646 A | * | 11/2000 | West et al. | 606/41 |
| 6,224,592 B1 | * | 5/2001 | Eggers et al. | 606/41 |
| 6,241,724 B1 | * | 6/2001 | Fleischman et al. | 606/41 |

FOREIGN PATENT DOCUMENTS

| DE | 3050386 C2 | 11/1981 |
|---|---|---|
| DE | 3510586 C2 | 2/1986 |
| DE | 3511107 C2 | 2/1986 |
| DE | 3838840 C2 | 5/1990 |
| DE | 3930451 A1 | 3/1991 |
| EP | 0246350 A1 | 11/1987 |
| GB | 2308979 A | 7/1997 |
| NL | 1004655 C | 8/1998 |
| WO | WO 92/02272 A1 | 2/1992 |
| WO | WO 95/10978 A1 | 4/1995 |

* cited by examiner

Primary Examiner—Linda C. M. Dvorak
Assistant Examiner—David M. Ruddy
(74) Attorney, Agent, or Firm—Woodard, Emhardt, Naughton, Moriarty & McNett LLP

(57) ABSTRACT

An apparatus for the high-frequency treatment of body tissue comprises a head (10) which is provided with at least one HF electrode (14a, 14b, 14c) of an electrically conductive material. Optionally one electrode (14a, 14b) can be brought into contact with the tissue (24) to be treated and electrically activated. In order to avoid undesired temperature peaks provisions are made that the head supporting the HF electrode or the HF electrodes, respectively, comprises highly heat conductive portions (12) in order to dissipate heat generating at the HF electrode or the HF electrodes, respectively, in particular in the proximal direction.

11 Claims, 5 Drawing Sheets

APPARATUS FOR THE HIGH-FREQUENCY TREATMENT OF BODY TISSUE

FIELD OF THE INVENTION

The invention relates to an apparatus for the high-frequency treatment of body tissue with a head which comprises at least one HF electrode of an electrically conductive material, which can be brought into contact with the tissue to be treated.

BACKGROUND OF THE INVENTION

Such an apparatus for the high-frequency treatment, in particular coagulation, is known from DE 3930451 A1. The head of the apparatus shown therein has a front electrode at the distal end and a rear electrode spaced therefrom in the proximal direction. An insulating ring of a synthetic material is arranged between the electrodes.

DE 3511107 C2 also describes an apparatus for the high-frequency coagulation of biological tissue. There, the legs of a pair of coagulation forceps is formed from an electrically conductive material.

In the apparatus for the high-frequency treatment of body tissue (HF coagulation apparatus) described in DE 3838840 C2, the head is formed by a jacket of poorly heat conducting steel, upon which an Al/Ag layer is applied as an electrode.

DE 3510586 C2 also describes a high-frequency surgical device. Therein a monopolar active electrode is provided which cooperates with a neutral electrode. Alternatively, a bipolar electrode is also provided.

With respect to the state of the art, reference is also made to the following documents: EP 0 246 350 A1; GB 2308979 A; DE 30 50 386 C2; and WO 95/10978 A1.

SUMMARY OF INVENTION

The present invention can be utilized both with monopolar electrodes and with bipolar electrodes.

In the following, the above mentioned state of the art is taken as known, in particular the electrical supply and the control of the the HF energy.

The present invention relates to a special configuration of the head of an HF surgical device. The term 'head' refers to that component by means of which the HF energy is coupled (transferred) into the body tissue to be treated. The head carries the HF electrodes. So-called cardiac catheters are special apparatuses for the high-frequency treatment of body tissue. The present invention relates in particular to such cardiac catheters as well.

In recent years, the development of the state of the art was directed in particular at increasing the volume of the tissue denaturated by means of HF energy. This applies in particular to the development of the so-called cardiac catheters. For this purpose, the active electrodes of the head have been enlarged. With an increasing electrode diameter and increasing electrode areas, the volume of the denaturated or coagulated, respectively, tissue could be increased. An increase of the HF energy emitted by the HF electrodes, however, is only possible to such a degree that the boundary layer between the HF electrode and the treated tissue does not exceed certain temperatures. The temperature generated in the contact zone between the electrode and the tissue in turn depends on how the generating heat is dissipated from this zone. The electrode itself plays an essential role in this heat dissipation. The tissue through which blood circulates and the blood flowing around the electrode, also dissipate heat. By enlarging the active electrode of the HF head, the contact area with the tissue and thus the cooling area can be enlarged. An increase of the electrode area, however, is not desired for a plurality of applications.

Another possibility of cooling would be the use of so-called active cooling systems such as, for example, flushing-of the electrode with a cooling liquid such as a saline solution. The cooling liquid could be introduced into the patient's blood stream through small openings in the electrode. This, however, will strain the blood circulation of the patient and increase the risk of infection. In addition, this will make handling of the HF device considerably more cumbersome.

Upon an increase of the electrode areas the blood or the tissue parts, respectively, will be largely heated in an uncontrolled manner by the emission of the HF energy, i.e. blood and tissue parts are heated considerably, for which this is not desired. The blood flowing around the electrode areas can start boiling. Via imaging methods (e.g. ultrasonics) an extreme formation of bubbles at portions of the electrode which were not in direct contact with the tissue to be treated was observed. Such a bubble formation in the blood or at tissue surfaces as well can lead to massive artefacts in the. ECG system during the cardiac ablation. A destruction of blood cells and a formation of coagel are also to be feared. In brain operations and operations on the heart (ablation technique) the phenomena described lead to a considerable interference of signals.

The invention is based on the object to further develop an apparatus for the high-frequency treatment of body tissue of the initially mentioned type in such a manner that a destruction of blood-cells and an undesired formation of coagel as well as blood clotting are avoided. In addition, the efficiency of the apparatus, i.e. the ratio of emitted HF energy to the desired denaturated tissue volume, is to be improved.

For the solution of these technical problems the invention provides for the head supporting the HF electrode to comprise highly heat conductive zones in order to dissipate heat generating at the HF electrode away from the electrode in the proximal direction, with the head having a length of 6 to 12 mm and a diameter of 1.5 to 4 mm.

Thereby the occurrence of temperature peaks near the electrode is prevented and the heat is dissipated away from the critical places. The heat dissipation can also be effected partially in the radial direction (relative to the longitudinal axis of the head).

The invention enables the use of relatively small active electrodes. This enables a precise derivation of small electrical nerve signals and a more precise locating of nerve paths or vessels, respectively. In addition, a high precision with respect to the site of the tissue impedance change during the HF emission is achieved. Furthermore, the invention enables an improvement of the derivation signal quality before and during the HF emission. Temperature measurement is also considerably improved, and the speed of temperature measurement in the active electrode is increased. Finally, the invention also enables an adaptation of the electrode areas to the tissue portions to be treated.

According to the invention, the active electrode of the head of the HF device is preferably no longer formed by a single solid metal body as in the state of the art, which homogeneously emits HF energy in all directions, but by one or several smaller conductive electrode areas which confine themselves to the respective desired emission zone. Thereby, a precisely controllable emission of HF energy into the tissue portion which is actually to be treated is possible. Blood and tissue portions which are not to be subjected to HF energy will be heated to a lesser extent. Cooling is improved by enlarging the overall surface of the head by an electrically insulating but a thermally highly conductive material. Thereby the active electrode area is cooled as well.

For example, the inventive head with the HF electrode or several HF electrodes can be manufactured in such a manner that the head is formed by a solid basic body of a thermally highly conductive material such as diamond or ceramic, onto which the active electrode areas are applied as layers, e.g. by vapour deposition. The active electrode areas can also be formed directly as temperature sensors (e.g. as thermocouples).

Alternatively, the inventive head may also be constructed in such a manner that it consists of a solid metal body which is highly heat conductive and onto which an electrically insulating but thermally highly conductive layer is applied. This layer may e.g. consist of silicon dioxide, diamond, or ceramic. The active electrodes can then be applied as layers as well onto the electrically insulating, thermally highly conductive layer.

The (half) ball-shaped electrode head provided by the invention as a whole has a smooth surface, and in the case of the formation of two or more electrode areas, these are immediately neighbouring with small insulating spacer strips, if required. Besides the electrode areas, the head comprises further areas which are formed by a highly heat conductive material in order to effectively dissipate the heat from the zone of the effective electrode areas into farther proximally situated zones of the system, where the heat is distributed over larger areas and volumes, thus preventing temperature peaks. According to preferred embodiments of the invention the electrodes can be applied as very thin layers onto a solid body. The layer thickness may be in the range of a few mm, e.g. <5 mm.

According to a preferred embodiment of the invention the head consists of at least one electrode and, with the exception of a relatively thin electrically insulating layer which may be provided, exclusively of a highly heat conductive material.

Further preferred embodiment of the invention are described in the dependent claims.

In particular, it is provided to arrange several HF electrodes at the distal end of the head, with the individual electrodes being capable of optionally being controlled individually or in combination, i.e. as required, one or the other electrode can be switched off so that it does not emit HF energy. With such a configuration of the head it is possible to activate only those HF electrodes which are actually positioned with respect to the tissue to be treated in such a manner that the energy emitted by them has the desired effect, while those electrodes which would only cause an undesired heating of blood and tissue are not activated.

The invention also teaches certain dimensions of the head and the electrodes in accordance with preferred embodiments.

BRIEF DESCRIPTION OF DRAWINGS

Embodiments of the invention will be described more detailed with reference to the drawing in which.

DETAILED DESCRIPTION OF THE INVENTION

Figure 1:
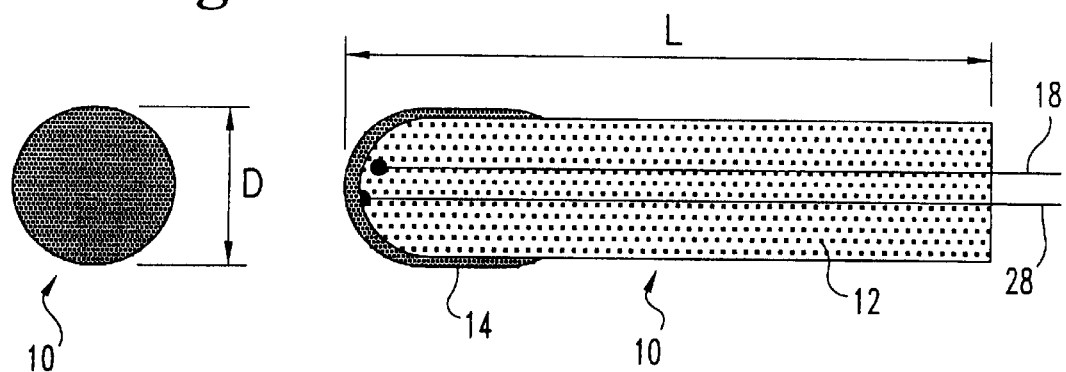
FIG. 1 shows a first embodiment of an apparatus for the high-frequency treatment of body tissue as an axial section and a front view.

FIG. 1 shows a head 10 for an HF treatment device. In the illustrated embodiment the head has a length L of approx. 8 mm and a diameter D of approx. 2 mm. At the distal end of the head 10 an HF electrode 14 is applied in the form of a metal layer to the body of the head. With the exception of the metallic HF electrode, the body of the head 10 thus consists of portions 12 of a highly heat conductive material, such as for example, diamond or ceramic with a high thermal conductivity. The portions 12 are not electrically conductive. The left side of FIG. 1 also shows a front view of the head 10. A temperature sensor which is known per se, e.g. a thermocouple, is inserted in the body of the head immediately proximally behind the HF electrode 14 and is connected via a line 18 with the control and supply means (not shown). The electrical line 28 for the HF electrode is also schematically shown in FIG. 1.

Figure 2:
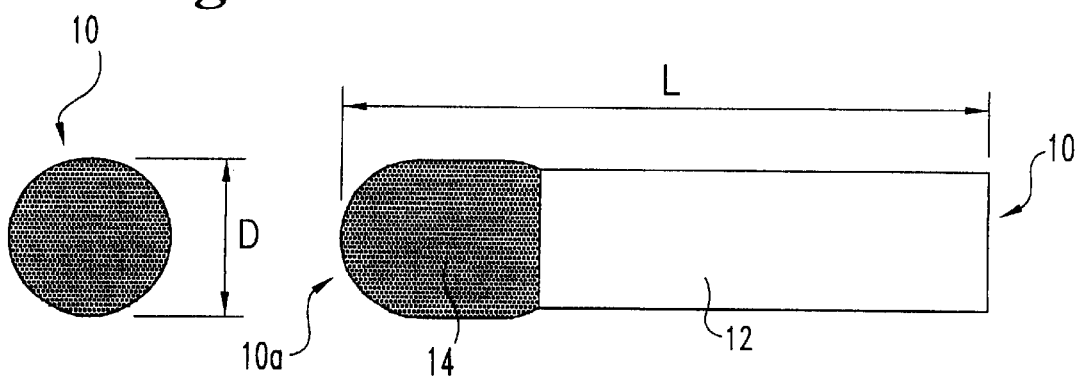
FIG. 2 shows the embodiment of FIG. 2 as a side view and a front view.

FIG. 2 shows the same apparatus as FIG. 1, but as a non sectioned side view.

Figure 3:
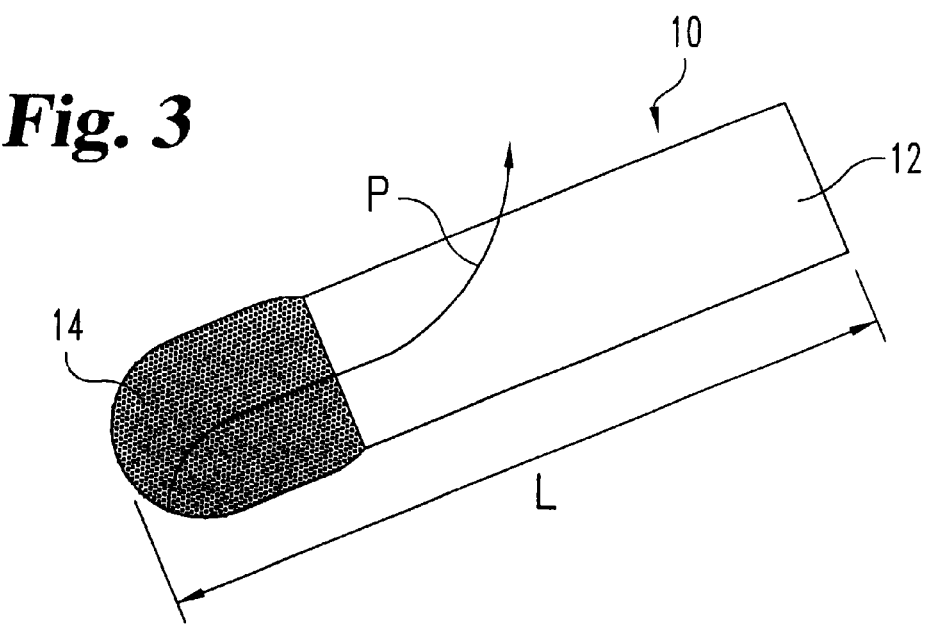
FIG. 3 shows the heat conduction in an apparatus according to FIGS. 1 and 2.

FIG. 3 shows the heat conduction in an HF apparatus according to FIGS. 1 and 2. As initially explained, heat is generated in particular on the surface of the HF electrode, which must be distributed in such a manner that unnecessary temperature peaks are avoided. The structure of the head, as previously described with reference to FIGS. 1 and 2, causes the heat generating in the zone of the HF electrode 14 to be dissipated to the rear, i.e. in the proximal direction via the portions 12 of the head 10 as indicated by the arrow P. A heat accumulation to the distal tip of the head 10 is thereby avoided.

Thus, it is prevented that at the so-called contact site in particular, i.e. in those zones in which the electrode is in contact with the tissue, an undesired temperature increase takes place. In the extreme case, such temperature peaks can even lead to the formation of gas (vapourizing water). With a continuing undesired temperature increase, the contact area in the tissue zone dehydrates whereby the electrical contact (the tissue impedance) can become very poor and the resistance of e.g. 50 Ohms can increase to more than 1 kiloohms.

Because of the described dissipation of the heat out of the metal tip into the heat conducting body 12 of the head 10 the surface of the electrode remains relatively cool. No unnecessary heating of body fluid or body tissue by the HF emission occurs in the rear portion (proximal portion) of the head 10, rather, the proximally rear portion of the head is provided for heat dissipation and cooling. The efficiency of the head, i.e. the ratio of the desired coagulation volume and HF energy is favourable.

Figure 4:
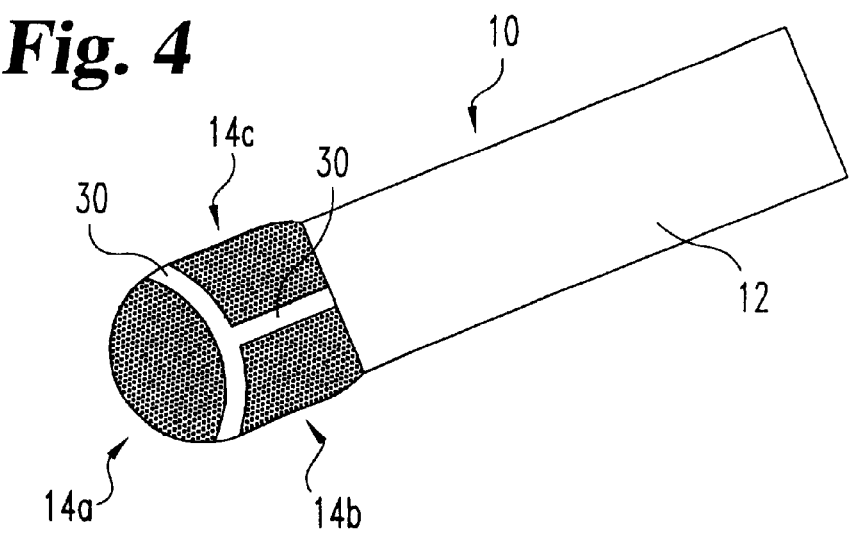
FIG. 4 shows another embodiment of an apparatus for the high-frequency treatment of body tissue.

FIG. 4 shows a further development of the embodiment according to FIGS. 1 to 3. In the apparatus for the HF treatment according to FIG. 4, three HF electrodes 14a, 14b, 14c are formed at the spherical distal end of the head 10. One electrode 14a is applied to the spherical tip in the form of a metal cap as a metal layer, and the two other electrodes 14b, 14c are formed immediately proximally behind it according to FIG. 4. When rotating the head 10 according to FIG. 4 about its longitudinal axis through 180°, the same illustration as in FIG. 4 will result. Between the electrodes 14a, 14b, and 14c narrow strips 30 from an electrically insulating material are formed. Like the material of the remaining portions 12 of the head 10, the material of the strips 30 is highly heat conductive.

The several electrodes, in the embodiment according to FIG. 4 three electrodes 14a, 14b, and 14c can optionally be activated individually, i.e. optionally one, two, or also all three electrodes can be supplied with current for the emission of HF energy, depending on the operating conditions of the device. This will be explained in more detail further below with reference to FIGS. 7 and 8.

Each of the individual electrodes 14a, 14b, and 14c are equipped with an own temperature sensor so that the temperatures which occur immediately at the electrodes or the electrode areas, respectively, can be measured essentially without corruption. In addition, at least one temperature sensor can be arranged in such a manner that it measures the temperature of the thermally highly heat conductive portions 12 of the head 10. These individual temperature sensors (e.g. thermocouples) are not shown explicitly in the figures. It is also possible to realize the temperature sensors by so-called thermistors. Alternatively, it is also possible to provide infrared detectors, fibre technical pick-ups, or temperature dependently oscillating elements as well as temperature sensors, which vary their colour reflection or colour radiation as a function of the temperature.

When using a thermocouple, two dissimilar metals which are contacting each other are used, e.g. gold and NiCr. This can for example be realized in the such a manner that the ceramic surface is vapour-deposited with palladium as an adhesive carrier and subsequently an NiCr layer is applied. The latter will be gold-coated. The interface between the NiCr layer and the gold layer forms the temperature sensor in the form of a plane sensor.

When using an infrared sensor, the temperature can be measured directly, i.e. as surface temperature. The infrared signal can be obtained via suitable IR conducting glass or quartz fibres even from extremely thin electrodes and transmitted to a more voluminous infrared detector.

The mentioned fibre technical pick-ups utilize a glass fibre which in the front area (so-called first end) is coated with temperature sensitive, fluorescent, or reflecting substances. These substances vary their colour reflecting or fluorescent properties as a function of the temperature. By the coupling in of light via the second end of the fibre the substances can be excited, for example, their reflecting property can be utilized.

It is also possible to perform the temperature measurement by means of changing the length of a short fibre. In this case, a small fibre head (1 to 2 mm long) is metal-coated at both ends. One end is provided with a semipermeable mirror. Via a coupled in ajustable laser beam the resonance of the metal-coated fibre head can be measured. A temperature change of the fibre head causes its length to change and thus its resonance as well.

Temperature dependently oscillating elements can be realized e.g. by quartz materials. Quartzes are grown for this purpose in such a manner that their thermal behaviour has an influence as great as possible on the natural resonance frequency.

As the material for the highly heat conductive portions 12 of the head 10 in particular ceramic materials, glass ceramic, silicon oxide, and diamond are considered. The HF electrodes are then applied two-dimensionally onto these materials as the basic material of the body of the head 10 or suitably embedded into this material.

Figure 5:
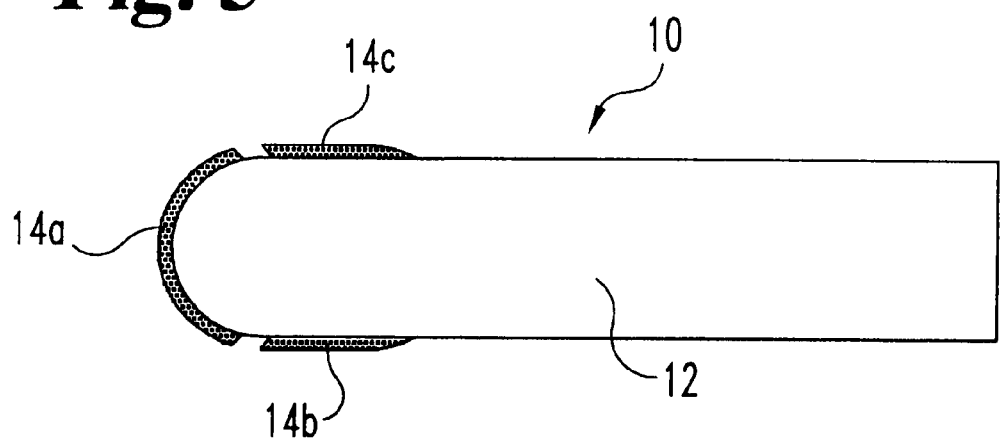
FIG. 5 shows a sectional view of the embodiment according to FIG. 4.

FIG. 5 is a sectional view of such a structure, with the body 12 of the head 10 consisting of a highly heat conductive but electrically insulating material, and the electrodes 14a, 14b, 14c being applied of an electrically conductive material in the form of a layer, e.g. by vapour deposition.

Figure 6:
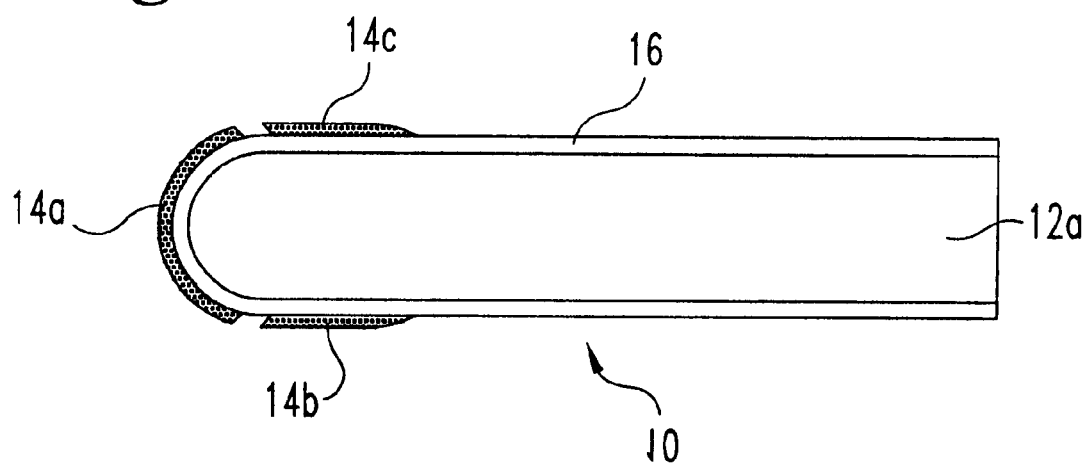
FIG. 6 shows a modification of the embodiment according to FIGS. 4 and 5.

FIG. 6 shows a modification of the previously described embodiments, with a main body 12a of the head 10 of highly heat conductive material, e.g. copper. Onto the heat conductive main body 12a a thin, electrically insulating layer 16 of a material which, however, also has good heat conducting properties, e.g. diamond or cermamic, is applied. Onto the electrically insulating layer 16 which has good heat conducting properties the electrodes 14a, 14b, 14c are applied as metallized areas, e.g. of platinum or gold.

Figure 7:
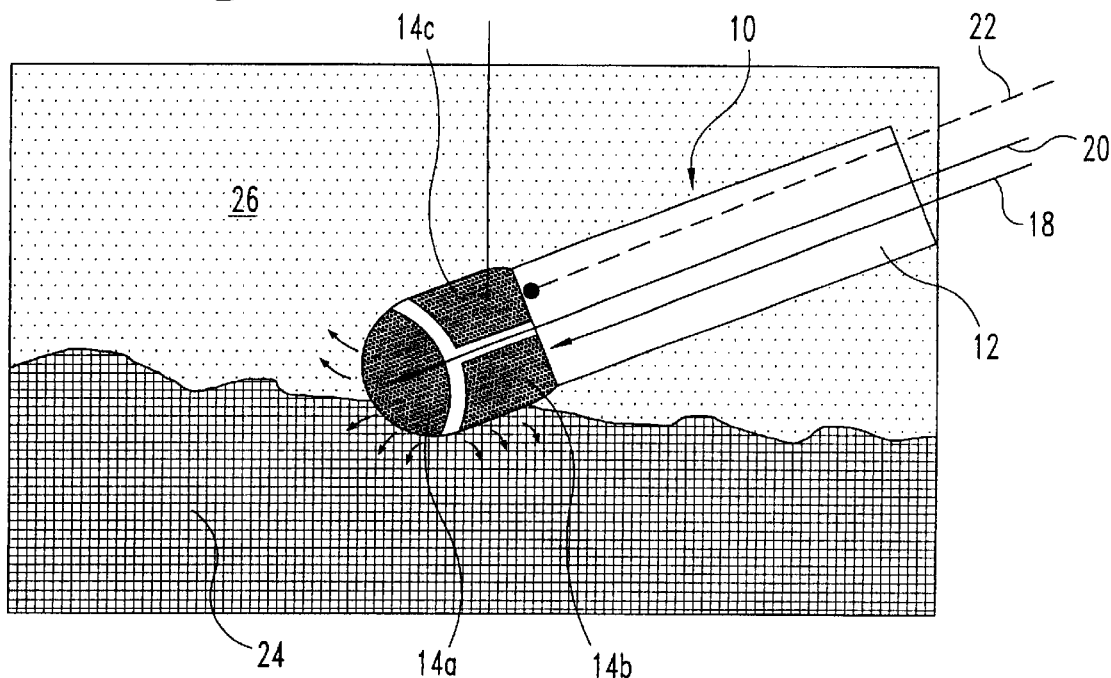
FIG. 7 shows the use of an apparatus according to FIGS. 4 to 6 in the high-frequency treatment of tissue.
Figure 8:
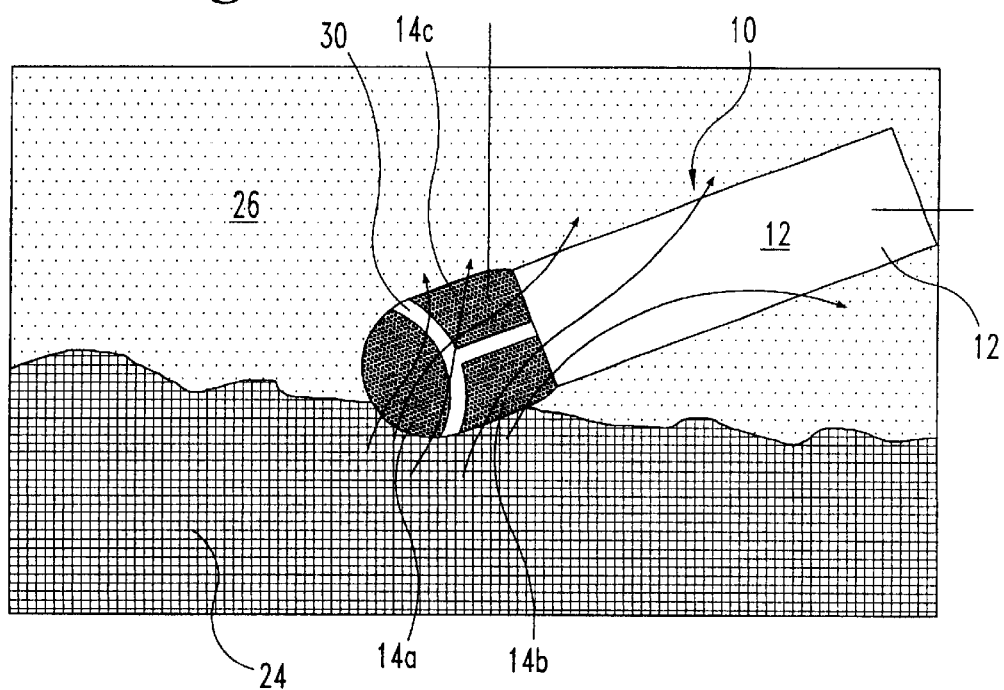
FIG. 8 shows the heat flow when using an apparatus according to FIG. 7.

FIGS. 7 and 8 explain the operation of an HF device according to FIGS. 4 to 6. Tissue 24, e.g. a cardiac wall, is to be treated by HF energy. The blood is indicated by reference numeral 26. As shown in FIG. 7 only the electrodes 14a and 14b are in direct contact with the tissue 24 to be treated. Therefore only the HF lines 18 and 20 are activated which supply current to the electrodes 14b and 14a, respectively. The generation and the transport of the HF energy is indicated in FIG. 7 by the small arrows which extend away from the activated electrodes 14a, 14b. The non-activated electrode 14c, the supply line 22 of which remains currentless, does not unnecessarily heat the surrounding blood 26.

FIG. 8 shows the heat transport schematically by way of the illustrated particles. As can be seen, not only the proximal portions 12 of the body 10 have a heat dissipating effect but also the non-activated electrode 14c and the electrically insulating strips 30 between the individual electrodes as well. In an HF treatment apparatus according to FIG. 6 the effect is similar to FIG. 8.

Figure 9:
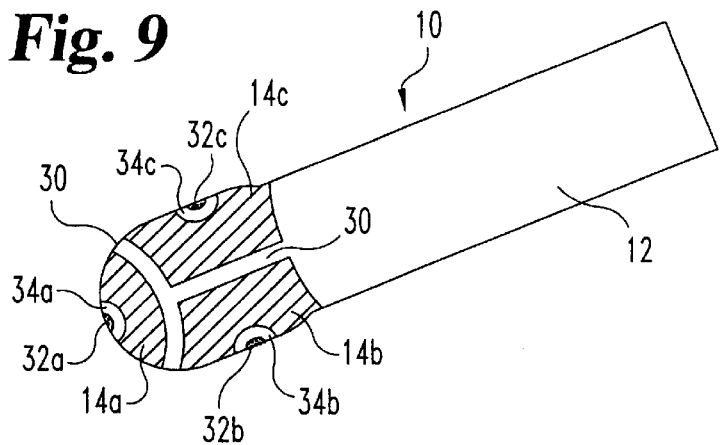
FIG. 9 shows a side view of another embodiment of an apparatus for the high-frequency treatment of body tissue.
Figure 10:
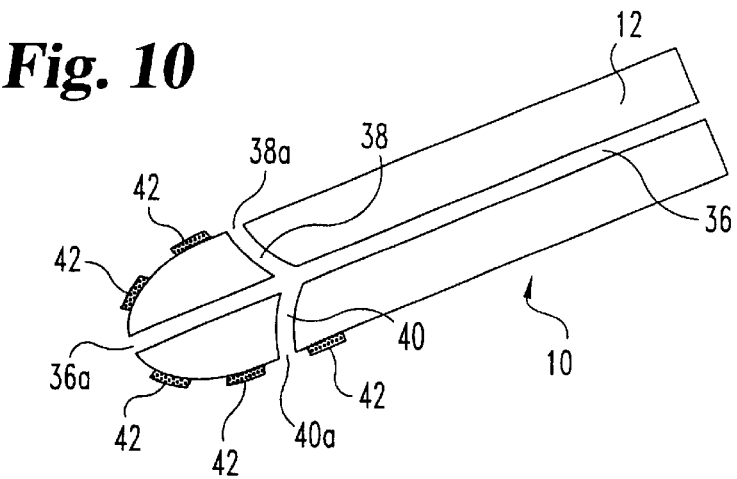
FIG. 10 shows a sectional view of another embodiment of an apparatus for the high-frequency treatment of body tissue.
Figure 11:
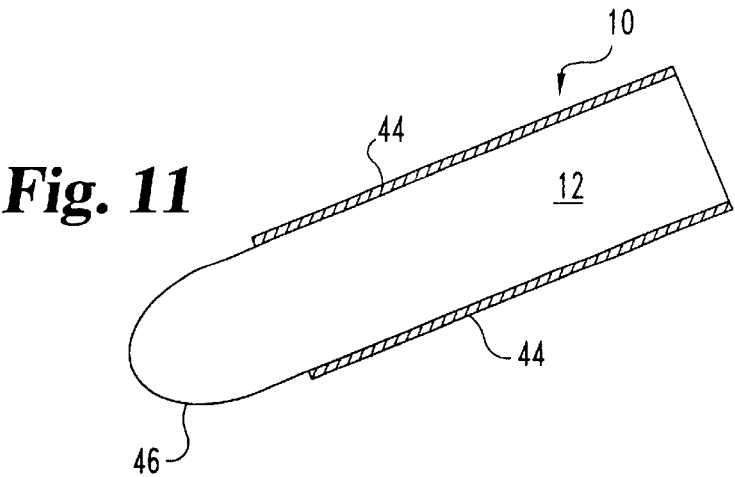
FIG. 11 shows still another embodiment of an apparatus for the high-frequency treatment of body tissue.

FIGS. 9, 10, and 11 show further embodiments of apparatuses for the HF treatment of body tissue.

The embodiment according to FIG. 9 is a further development of the previously described embodiments in that the head is further cooled by an internal cooling system. For the cooling of the head ducts are formed in the head 10 through which a cooling liquid flows. The cooling liquid can flow through the head without leaving same. However, according to the embodiment of FIG. 9 it is also possible to have the cooling liquid leave the head through openings 32a, 32b, 32c. Each of the openings 32a, 32b, and 32c are arranged approximately centrally in the electrodes 14a, 14b, and 14c, respectively. Each hole is surrounded by areas 34a, 34b, and 34c of an electrically insulating material. Said insulating material is, however, highly heat conductive.

FIG. 10 shows a similar cooling arrangement for an HF head 10 as a sectional view. The ducts for cooling are assigned reference numerals 36, 38, and 40, respectively; the openings of the ducts have reference numerals 36a, 38a, and 40a, respectively. As in the previously described embodiments, the electrodes of this embodiment can be very thin vapour deposited layers. In the figures, the layer thicknesses are shown in a highly magnified form for purposes of definition. The layer thickness of the electrodes 42 can, for example, be only a few mm, in particular, less than 10 mm and, particularly preferred, less than 4 mm.

With modern solid state technique it is possible to form zones in a single body, which have different electrical conductivity capabilities. In diamond, for example, electrically conductive and electrically non-conductive zones can be generated during its growth by doping it with different atoms. In this manner, even electrode zones and supply lines to the electrodes can be integrally formed in a growing diamond crystal.

FIG. 11 shows another embodiment, wherein the head 10 as a whole consists of a metal onto which an electrically insulating layer 44, however, with a very good thermal conductivity, is applied. The distal tip 46 of the metal body serves as the conducting HF electrode.

Special aspects of the above described invention can be summarized as follows:

At least one HF electrode of the HF apparatus is arranged at the distal end of the head.

Further, it can be provided for forming the head cylindrical with a spherical distal tip 10a.

In addition, two or more electrodes (14a, 14b, 14c) are provided at the head (10), which can optionally be activated. It can also be provided for the HF electrode (14) or the HF electrodes (14a, 14b, 14c), respectively, to be applied on a body of a conductive material, if required, with an electrically insulating layer (16) in between.

It can be provided for the HF electrode or the HF electrodes, respectively, to be arranged in a section of 1 to 6 mm, preferably of 2 to 4 mm, of the longitudinal extension of the head in the area of its distal end.

Another aspect of the invention is, in particular, that three or more HF electrodes (14a, 14b, 14c) are arranged at the head (10), one of which at the distal end (10a) and the other electrodes proxially behind same.

Another configuration provides for a temperature sensor or several temperature sensors in order to measure the temperature of the thermally highly conductive portion (12) of the head (10).

The temperature sensor or the temperature sensors, respectively can be formed by thermocouples.

As temperature sensors thermistors can be provided as well.

In addition, it can be provided for at least one of the temperature sensors to be formed by an infrared detector or a fibre technical pick-up, or by temperature dependently oscillating elements, with the latter varying their colour reflection or colour radiation as a function of the temperature.

Another aspect of the invention is that the body 12 of the head as well as the HF electrodes are formed from metal, with the HF electrodes being separated by electrically insulating strips (30) or layers (16), respectively, from the body (12a), with the latter being formed of a thermally highly conductive material, e.g. copper.

In addition, it can be provided for the effective surfaces of the electrically conductive HF electrodes to be reduced by applying an electrically insulating material.

In addition, a cooling system with a flowing cooling medium can be provided inside the head.

The cooling liquid can escape the head to the outside through one or several openings.

In addition, it can be provided for several additional electrodes to be arranged in the proximal direction, which in turn can be divided into partial segments.

What is claimed is:

1. An apparatus for the high-frequency treatment of body tissue with a head (10), the head comprising a distal tip portion and at least one HF electrode (14) of an electrically conductive material, which can be brought into contact with the tissue (24) to be treated, wherein the head (10) supporting the HF electrode (14) is formed of a thermally highly conductive material onto which at least one electrode (14) is formed, wherein the head (10) comprises highly heat conductive portions (12) in order to dissipate the heat generating at the HF electrode (14) in the proximal direction, with the head (10) having a length of 6 to 12 mm and a diameter of 1.5 to 4 mm, wherein all HF electrodes (14, 14a, 14b, 14c) are arranged on the proximal side of the tip in a section of 1 to 6 mm of the longitudinal extension of the head (10), and the distal tip portion and the highly heat conductive portions include a highly heat conductive material.

2. The apparatus according to claim 1 characterized in that the portions (12) of the head of a highly heat conductive material have a heat dissipating surface which is 0.3 to 10 times the effective surface of said at least one HF electrode (14) or of the HF electrodes (14a, 14b, 14c).

3. The apparatus according to claim 1 characterized in that the highly conductive portions (12) include an electrically insulating material.

4. The apparatus according to claim 1 characterized in that the head has a length of 7 to 10 mm.

5. The apparatus according to claim 1 characterized in that the head has a diameter of 1.5 to 3 mm.

6. The apparatus according to claim 1, characterized in that at least one electrode (14) is arranged in the area of the tip (10a) of the head (10).

7. The apparatus according to claim 1, characterized in that the portions of the head of a highly heat conductive material have a heat dissipating surface which is 1 to 2 times the effective surface of the HF electrode (14) or the HF electrodes (14a, 14b, 14c).

8. The apparatus according to claim 1, characterized in that the highly heat conductive portions (12) of the head (10) are comprised of diamond or ceramic.

9. The apparatus according to claim 1, characterized in that each of the one HF electrode (14) or of the several HF electrodes (14a, 14b, 14c) is provided with a temperature sensor.

10. The apparatus according to claim 1, characterized in that an additional HF electrode is provided in the proximal direction, said additional electrode being capable of being divided into individually controllable segments.

11. The apparatus according to claim 1, characterized in that the HF electrodes are arranged in a section of 2 to 4 mm of the longitudinal extension of the head in the area of its distal end.

* * * * *